United States Patent [19]

Petersen

[11] 4,394,314

[45] Jul. 19, 1983

[54] PROCESS OF PREPARING AROMATIC ALDEHYDES BY REACTING SELECTED AROMATIC COMPOUNDS WITH FORMAMIDINE ACETATE AND AN ORGANIC ACID ANHYDRIDE

[75] Inventor: Wallace C. Petersen, Wilmington, Del.

[73] Assignee: E. I. Du Pont de Nemours and Company, Wilmington, Del.

[21] Appl. No.: 256,734

[22] Filed: Apr. 23, 1981

[51] Int. Cl.³ .................... C09B 11/14; C07C 103/24
[52] U.S. Cl. ............................ 260/391; 260/465 D;
544/159; 548/262; 548/363; 548/455; 548/496;
549/59; 549/76; 564/153; 564/155; 564/157;
564/158; 567/211; 567/212; 567/217; 567/218;
564/220; 564/221; 564/222; 564/223; 564/414;
564/305; 568/435; 548/561
[58] Field of Search ............. 564/153, 155, 157, 158,
564/211, 212, 218, 220, 221, 222, 217, 223, 414,
436; 568/435; 260/326.13 D, 326.43, 347.3,
391, 465 D; 544/159; 548/363, 262; 549/59, 76

[56] References Cited

PUBLICATIONS

R. Kahn and H. A. Staab, Ber. 87 272 (1954).
F. B. Dains, Ber. 35 2504 (1902).
J. B. Shoesmith and J. Haldane, J. Chem. Soc. 2704 (1923).

Primary Examiner—Thomas A. Waltz

[57] ABSTRACT

A process of reacting a ring carbon atom of an aromatic compound Ar with a compound of the formula $H_2NCH=NH_2{}^+CH_3CO_2{}^-$, and an anhydride which has the formula $(CH_3C)_2O$, $(ClCH_2C)_2O$, $(CH_3CH_2C)_2O$,

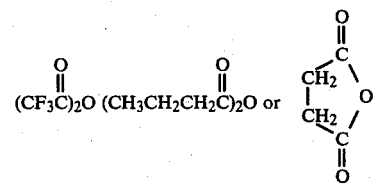

at from 10° to 200° C. and preferably 25° to 40° C. to form a compound of the formula

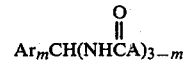

where m is 1, 2 or 3, and A is H or F. In the case where m is 1 the compound

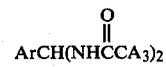

can be hydrolyzed to ArCHO. Additionally, Fischers base can be reacted with formamidine acetate to form

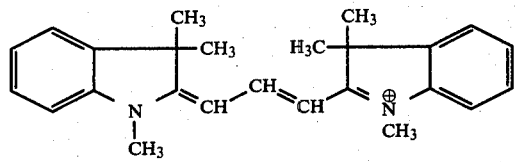

12 Claims, No Drawings

PROCESS OF PREPARING AROMATIC ALDEHYDES BY REACTING SELECTED AROMATIC COMPOUNDS WITH FORMAMIDINE ACETATE AND AN ORGANIC ACID ANHYDRIDE

BACKGROUND OF THE INVENTION

1. Field of the Invention

The present invention relates to a process for the synthesis of aromatic aldehydes from highly reactive aromatic starting compounds by treating the aromatic starting compound with formamidine acetate and an acid anhydride to produce an aromatic aldehyde bisacylaminal which yields the aldehyde on hydrolysis in aqueous acid.

At present the Vilsmeier-Hack reaction is generally used to produce such aldehydes. The Valsmeier-Hack reaction uses $POCl_3$ and dimethyl formamide as the active reagents and the reaction is sensitive to temperature control. If the reaction has an uncontrolled exotherm, dimethylcarbamoyl chloride, which is carcinogenic, may be generated. Further, the products often require purification before use in dye manufacture. Also, large amounts of $H_3PO_4$ are formed which must be disposed of.

2. Description of the Prior Art

The reaction of diphenylformamidine with aromatic phenols in aqueous acid solution to produce aldehydes is known. R. Kahn and H. A. Staab, Ber. 87 272 (1954); F. B. Dains, Ber. 35 2504 (1902); J. B. Shoesmith and J. Haldane, J. Chem. Soc. 2704 (1923).

SUMMARY OF THE INVENTION

The present invention involves reacting a reactive aromatic compound such as N,N-dimethylaniline to form an aldehyde as follows:

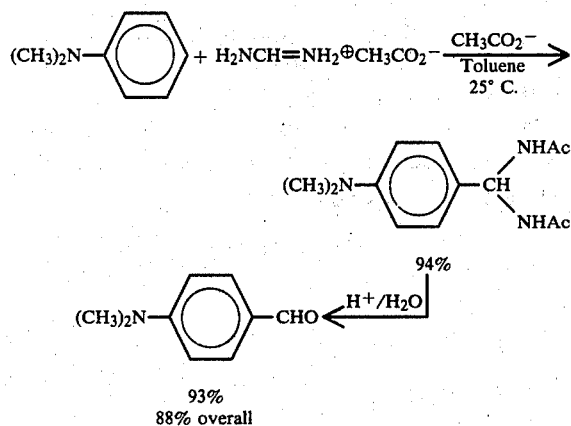

93%
88% overall

The aldehyde produced has utility in the preparation of various dyestuffs through condensaton reactions. Alternatively the N,N'-[p-(dimethylamino)benzylidine]-bisacetamide may be reacted directly with various compounds such as an enamine to form various compounds such as dyestuffs. Alternatively the N,N'-[p-(dimethylamino)benzylidene]-bisacetamide can be reacted with 1 or 2 moles of a compound such as N,N-dimethyl aniline to form

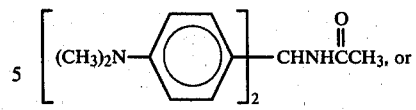

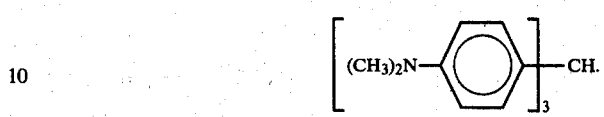

DETAILED DESCRIPTION

The present invention is applicable to aromatic starting compounds generally. Generally, the starting compounds are highly reactive secondary or tertiary aromatic amines. Such preferred amines have the formula

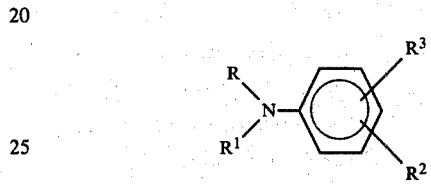

where —R is —$CH_3$, —$C_2H_5$, —$CH_2CH_2CN$, —$CH_2C-H_2OH$, —$CH_2CH_2OCH_3$, —$CH_2CH_2N(CH_3)_2$, or —$CH_2CH=CH_2$; and —$R^1$ is —R or

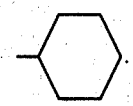

R and $R^1$ may be the same or different. —$R^2$ is —H, —$CH_3$ —$C_2H_5$, —$OCH_3$, —$OC_2H_5$ or

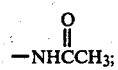

and —$R^3$ is H—$CH_3$, —$OCH_3$, or —$OC_2H_5$. The reactive site on the ring is para to the amine substituent. Suitable non-amino aromatic starting compounds include the following where the * indicates the reactive site.

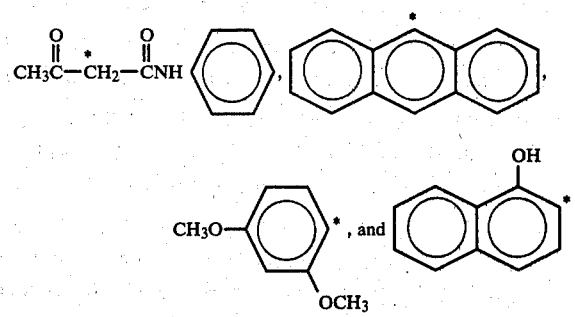

Various heterocyclic compounds are suitable for use as starting compounds in the present invention. Such heterocyclic compounds include the following where the * indicates the reactive site

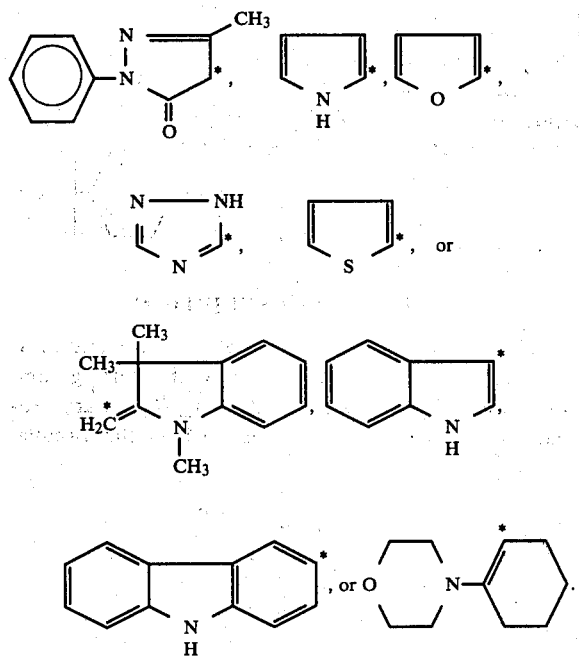

Generally, the reaction will be carried out at from 10° to 200° C. with from 25° to 40° C. being the preferred range. Most of the active aromatic components will react with the activated formamidine at ambient temperature in which case that is preferred. Since the reaction is generally exothermic the use of starting materials at ambient temperature will result in a reaction temperature of 25° to 40° C. In cases where the reaction is unduly slow at ambient temperature the use of an elevated temperature such as 100° to 200° C. may be employed.

Generally, the reaction is carried out in the presence of an organic solvent. The aldehyde derivatives of greatest interest in the production of dyes are obtained in the highest yield from reactions in nonpolar solvents (toluene, xylene, chlorobenzene) at 25° to 40° C. The animals have poor solubility in these solvents and precipitate in pure form. Formamidine acetate also has poor solubility in nonpolar solvents and this results in the desired slow consumption of reagent. When using these solvents the product is a very high melting fluffy white solid which thickens in the course of the reaction and allows easy isolation and high purity of the product. The use of a polar-aprotic solvent such as dimethyl formamide in order to reduce the thickness gives a considerable yield of a byproduct. Under the proper conditions a high yield can be obtained of the condensation product of 2 moles of dimethylaniline and 1 mole of formamidine acetate [bis-(p-dimethylaminophenyl)methylacetamide]. A 68% yield, based on dimethylaniline, was obtained even with a stoichiometric mismatch of dimethylaniline and formamidine acetate (1:1).

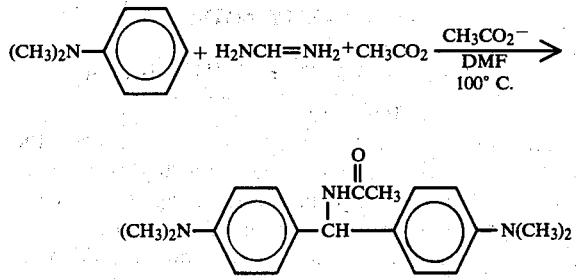

Though the electrophilic characteristics of the formyl carbon are greatly reduced by the attached p-dimethylaminophenyl group, under the proper conditions of polarity and temperature it is still an active electrophilic reagent. The use of acetic acid as a solvent and 3 moles of dimethylaniline with 1 mole of formamidine acetate to make leuco Crystal Violet indicates that leuco triarylmethane dyes can be prepared readily by control of reaction conditions. Thus, the initial reaction step of the present invention can best be described as the reaction of a ring carbon atom of an aromatic organic compound as with a compound of the type:

$$H_2NCH=NH_2{}^+CH_3CO_2{}^-,$$

and an anhydride which has the formula

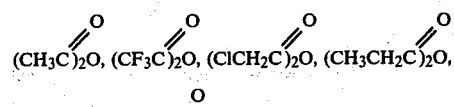

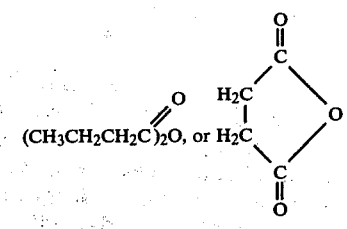

to form a compound of the formula $$Ar_mCH(NHCCA_3)(3-m)$$

where m is 1, 2 or 3, and —A is —H or —F.

The overall reactions of the present invention can be described by the following outline, when using acetic acid and acetic anhydride.

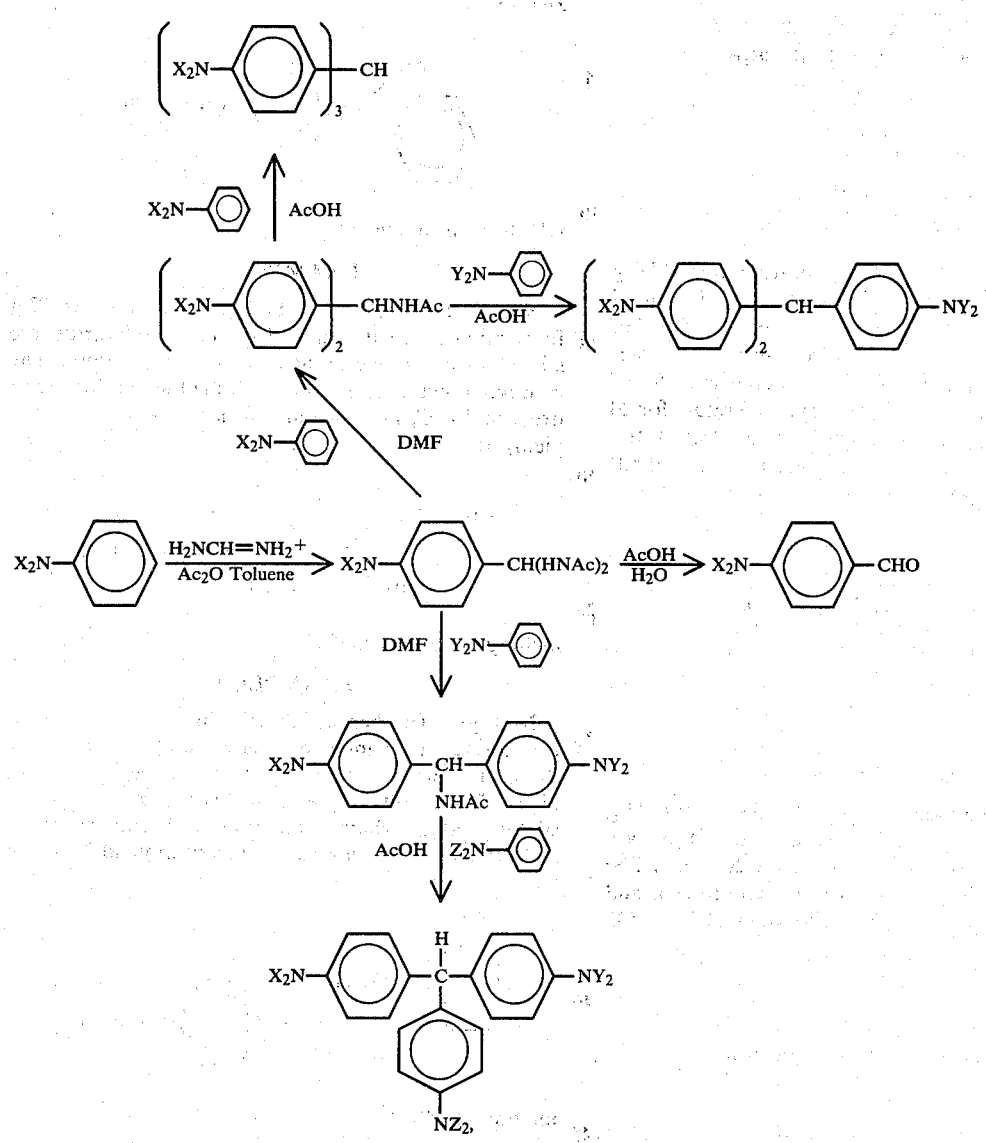

where —Ac is

and X, Y and Z are R or $R^1$ as defined above.

DESCRIPTION OF THE PREFERRED EMBODIMENTS

EXAMPLE 1

Dimethylaniline (12.1 g), 100 ml toluene, 25 g acetic anhydride and 11 g of formamidine acetate are stirred together under a nitrogen blanket at room temperature. The precipitate which formed is filtered and dried to yield 23.5 g (94.4% yield) of

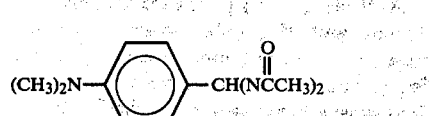

(m.p. 258°–260° C.).

EXAMPLE 2

Toluene (100 ml), 20.6 g of

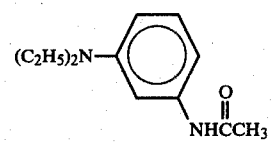

and 11 g of formamidine acetate are stirred at room temperature for 18 hours. The resulting precipitate is filtered and dried in a vacuum oven at 50° C. to yield 28.6 g (85.4% yield) of

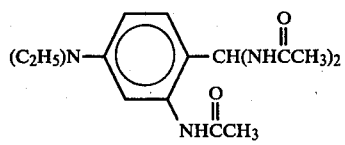

which has a melting point of 210° C.

EXAMPLE 3

(N-cyanoethyl)(N-hydroxyethyl)-m-toluidine (37.4 g of a 54.6% by weight solution in acetic acid) is poured into 200 ml of water and extracted 3 times with 50 ml of toluene. The toluene solution is dried over sodium sulfate, mixed with 11 g of formamidine acetate and 25 g of acetic anhydride, and stirred at room temperature for 20 hours. The precipitate is filtered on a cloth filter, washed with toluene and dried in a vacuum oven at 50° C. to yield 16.1 g (48.5% yield) of a waxy material of the formula

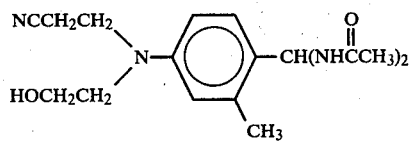

EXAMPLE 4

N,N-diethyl-m-toluidine (16.3 g), 150 ml toluene, 11 g formamidine acetate, and 25 g acetic anhydride are stirred together at room temperature for 20 hours. The resulting precipitate is filtered, washed with toluene and dried in a vacuum oven at 50° C. to yield 24.7 g (85% yield) of

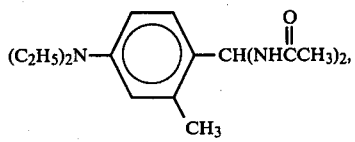

melting at 229° to 230° C.

EXAMPLE 5

N-ethyl-N-(2-methoxyethyl)aniline (5.45 g), 50 ml toluene, 3.5 g formamidine acetate and 8 g acetic anhydride are stirred together overnight. The resulting precipitate was filtered, washed with toluene and dried in a vacuum oven to yield 6.9 g (74% yield) of

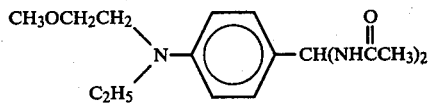

mp 178–9° C.

EXAMPLE 6

N-methyldiphenylamine (18.3 g), 125 ml toluene, 12 g formamidine acetate and 25 g acetic anhydride are stirred together overnight at room temperature. The resulting precipitate is filtered, washed with toluene and dried in a vacuum oven at 50° C. to yield 27.4 g (88% yield) of

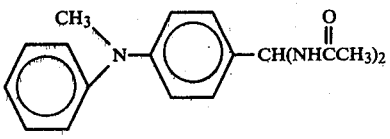

which melts at 214° to 216° C.

EXAMPLE 7

N-allyl-N-methylaniline (14.7 g), 125 ml toluene, 12 g formamidine acetate and 25 g acetic anhydride are stirred together overnight at room temperature. The resulting precipitate is filtered, washed with toluene and dried at 50° C. in a vacuum oven to yield 25 g (91% yield) of

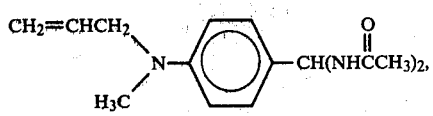

melting at 198° to 199° C.

EXAMPLE 8

N-ethyl-N-($\beta$-phenoxyethyl)aniline (24.1 g), 125 ml toluene, 12 g formamidine acetate and 25 g acetic anhydride are stirred together at room temperature overnight. The resulting precipitate is filtered to yield a sticky product which is recrystallized from methanol and dried at 50° C. in a vacuum oven to yield 21.4% of

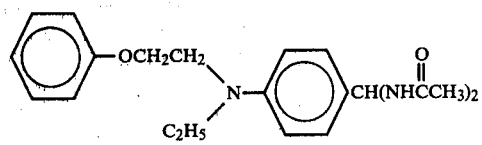

melting at 240° C.

EXAMPLE 9

Formamidine acetate (6 g), 6.9 g 1,3-dimethoxybenzene, 100 ml toluene and 23 g trifluoroacetic anhydride are stirred together. After 2 hours the mixture thickened and turned dark. The mixture is filtered and washed with toluene to yield 5.8 g (31% yield) of

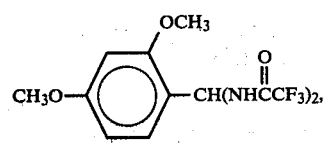

mp 164° C.

EXAMPLE 10

Anthracene (9 g), 100 ml toluene, 6 g formamidine acetate and 25 g trifluoroacetic anhydride are stirred together at room temperature for 20 hours. The resulting product is filtered under a nitrogen blanket, washed first with toluene and then with hexane and dried under a nitrogen blanket to produce 14.5 g of a material which on heating evaporates solvent and melts at 179° to 183° C. to form a red-brown melt. Chromatographic separation from untreated anthracene

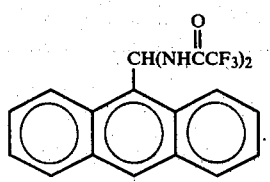

gave the pure product

EXAMPLE 11

1-phenyl-3-methylpyrazolone (17.4 g), 11 g formamidine acetate, 100 ml toluene and 25 g acetic anhydride are stirred at room temperature for 7 hours and then allowed to stand over a weekend. The precipitate which formed is then filtered, washed with toluene and dried at 50° C. in a vacuum oven to yield 7.05 g (23.5% yield) of

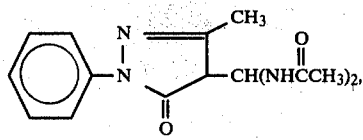

a yellow solid melting at 125° to 130° C.

EXAMPLE 12

Pyrrole (6.7 g), 11 g formamidine acetate, 100 cc toluene and 25 g acetic anhydride are stirred together for 15 hours at room temperature under a nitrogen blanket. The resulting precipitate is filtered, washed with toluene and dried in a vacuum oven at 50° C. to yield 14.5 g (74.4% yield) of

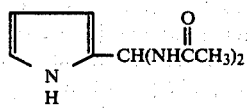

which melts at 153° to 154° C.

EXAMPLE 13

Indole (11.7 g), 100 ml toluene, 12 g formamidine acetate and 25 g acetic anhydride are stirred together at room temperature overnight. The resulting precipitate is filtered, washed with toluene and dried in a vacuum oven at 50° C. to yield 21.1 g (86% yield) of

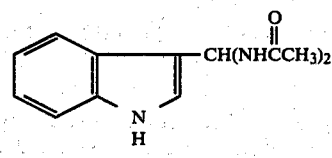

a white crystalline material melting at 221° to 222° C.

EXAMPLE 14

N-dimethylaniline (12.1 g), 100 ml dimethylformamide and 10.4 g formamidine acetate are mixed together and heated to 100° C. Acetic anhydride (22 g) is added all at once and the temperature rises to 110° C. The temperature is held at 100° C. for 1 hour after which the material is cooled to room temperature and drowned in a mixture of 500 ml of water and 20 ml of 30% aqueous sodium hydroxide. The material is filtered on a vacuum funnel, washed alkali-free with water and dried with the vacuum. The material is finally dried in a vacuum oven at 50° C. to yield 10.5 g (84.5% yield) of

which melts at 170° to 178° C.

EXAMPLE 15

A 250 cc flask fitted with an agitator, condenser, thermometer, nitrogen gas inlet and a dropping funnel is charged with 15 g N,N-diethylaniline, 50 ml acetic acid and 10 g acetic anhydride. The contents of the flask are heated to 100° C. and blanketed with nitrogen. Formamidine acetate (3.8 g) in 50 ml acetic acid is added dropwise over a period of 1 hour. The resulting mixture is held at 100° C. for 2 hours, after the addition of formamidine acetate in acetic acid is completed, and then cooled to room temperature. The contents of the flask are drowned in 200 ml of aqueous ammonium hydroxide and ice. The sticky precipitate which forms is extracted with 150 ml methylene chloride. The ethylene chloride solution is dried over sodium sulfate. The methylene chloride is stripped off in a Rotovac to yield 2.2 g of

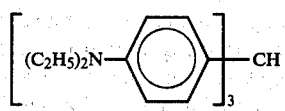

crystals melting at 175° C.

EXAMPLE 16

Toluene (100 ml), 20.6 g 3'-diethylaminoacetanilide

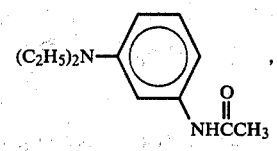

25 g acetic anhydride and 11 g formamidine acetate are stirred together at room temperature for 18 hours. The mixture is filtered and the solid obtained dried at 50° C. in a vacuum oven to yield 28.6 g of a solid melting at 210° C. The filtrate is heated to evaporate the solvent leaving

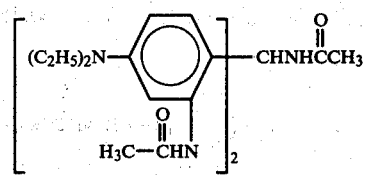

which melts at 65° to 66° C.

EXAMPLE 17

( Toluene 100 ml), 18.8 g N-ethyl-N-(2-cyanoethyl-m-toluidine)

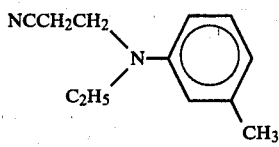

and 25 g acetic anhydride are heated to 100° C. and 11 g of formamidine acetate is added in portions. There is no rise in temperature. The mixture is held at 100° C. for 1 hour after the last addition of formamidine acetate and then cooled to room temperature. Hexane (100 ml) is added to the mixture which is then cooled with ice and filtered. The solid on the filter is washed with hexane and dried in a vacuum oven at 50° C. to yield 29.4 g of

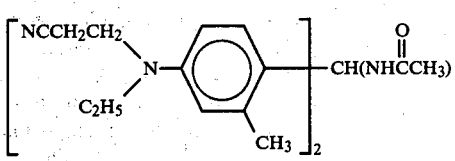

which melts at 72° to 75° C.

EXAMPLE 18

Acetic acid (150 cc), 34.8 g 1-phenyl-3-methylpyrazolone, 11 g formamidine acetate and 50 g of acetic anhydride are stirred together at room temperature for 2 hours, during which time no reaction takes place. The temperature is raised to 100° C. for 3 hours. On cooling crystals form at 85° C. The crystals are filtered, washed with a small amount of acetic acid and dried in a vacuum oven at 50° C. to yield 20.9 g of

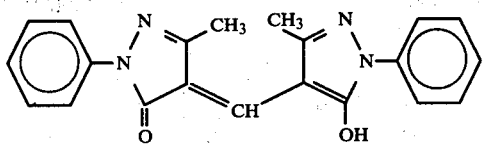

which melts at 182° to 184° C. Adding 150 cc water to the filtrate from above, followed by filtering and drying in a vacuum oven yields an additional 2.1 g of product.

EXAMPLE 19

Diethylaniline (14.9 g), toluene 100 ml, 11 g formamidine acetate and 25 g acetate anhydride are stirred together overnight at room temperature under a nitrogen blanket. The toluene slurry is then filtered, washed with toluene and dried to yield 23.0 g (83% yield) of

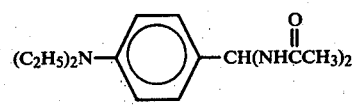

which melts at 220° to 222° C.

EXAMPLE 20

N-Cyanoethyl-N-ethylaniline (16 g), 100 ml toluene, 25 g acetic anhydride and 11 g formamidine acetate are stirred overnight under a nitrogen blanket. The resulting slurry is filtered and dried to yield 23.3 g of

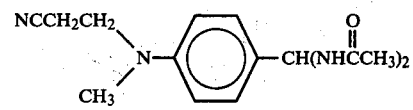

which melts at 186° to 192° C.

EXAMPLE 21

N-Cyanoethyl-N-ethyl-m-toluidine (18.8 g), 100 ml toluene, 11 g formamidine acetate and 25 g acetic anhydride are stirred together overnight at room temperature under a nitrogen blanket. The resulting slurry is filtered and dried to yield 29.5 g (93% yield of

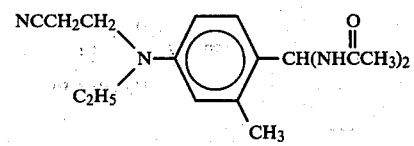

which melts at 190° to 192° C.

EXAMPLE 22

A. Preparation of formamidine acetate

Triethyl orthoformate (356 g, 2.40 mole), acetic acid (60 g, 2.633 mole) in 2500 ml toluene are heated to reflux and gaseous ammonia passed into the mixture until 82 g has been added. Ethanol distills while the ammonia is being passed into the reaction. After the ethanol has stopped distilling, the toluene/acetic acid azeotrope begins to distill at 105° C. and the excess ammonia is detected above the reaction mixture.

B. Reaction of formamidine acetate with diethyl aniline

Toluene (340 g), 305 g (2.06 mole) diethylaniline and 500 g acetic acid are added to the flask containing the formamidine acetate prepared above. The reaction mixture is held at 23° to 25° C. for 23 hours under a nitrogen blanket. After approximately 3 hours the reaction mixture becoes very thick but thins overnight and becomes light pink in color. The reaction mixture is filtered and the filter cake is dried in a vacuum oven at 50° C. to yield 423.2 g or 74.7% yield of the aminal

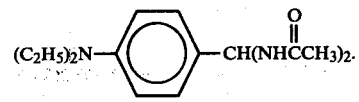

C. Hydrolysis to p-diethylaminobenzaldehyde

The aminal (19 g), prepared as described in (B) above, is added to a mixture of 500 ml of water and 25 ml concentrated hydrochloric acid with good agitation. The resulting mixture is heated to 50° C. and held at that temperature for 2 hours. Then the reaction mixture is cooled to room temperature and 30 ml of 30% aqueous sodium hydroxide is added with stirring. After stirring for an additional hour, the mixture is filtered and the filter cake washed alkali-free with water. The product is dried in a 50° C. vacuum oven to yield 10.6 g (93.23% yield) of p-diethylaminobenzaldehyde.

EXAMPLE 23

Dimethylaniline (12.1 g), 100 ml dimethylformamide, and 10.4 g formamidine acetate are heated to 100° C. Acetic anhydride (22 g) is added all at once. The temperature rises to 110° C. Everything is in solution. The temperature is held at 200° C. for 1 hour after which time the solution is cooled to room temperature and drowned in a mixture of 500 ml water and 20 ml of aqueous 30% sodium hydroxide. The resulting mixture is filtered on a suction filter, washed free of alkali with water and pulled dry on the filter. The resulting material is dried in a vacuum oven at 50° C. to provide 10.5 g of a material melting at 176° to 178° C., which is analyzed and found to have the structure

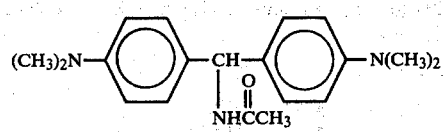

EXAMPLE 24

A solution is prepared from 121 g (1.0 mole) dimethylaniline, 90 g acetic anhydride and 100 g acetic acid. This solution is heated to 100° C. under a nitrogen blanket and then 38 g (0.365 mole) formamidine acetate is added in 5-gram portions over a period of 1.5 hours. The reaction mixture is held at 100° C. for an additional 2 hours and then cooled to room temperature. It is then drowned into 1 liter of water, 300 ml of concentrated ammonium hydroxide is added and the resulting slurry is stirred until it has cooled to room temperature. The product is filtered, the filter cake is washed with water until alkali-free and then dried in a vacuum oven at 50° C. The yield is 123.7 g (99.5% of theory). In a thin layer chromatogram only the product

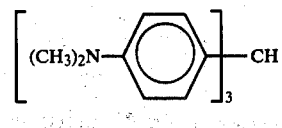

is detected.

EXAMPLE 25

A. Preparation of Crystal Violet

A premix is prepared from 10 g

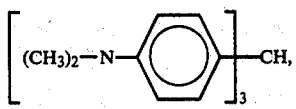

50 g acetic acid, 50 g acetamide, 0.2 g cuprous chloride, 5 ml acetone, 8 drops concentrated hydrochloric acid, 0.4 g chloranil and 4 ml water. This mixture is stirred and heated at 50° C. for 4 hours under a nitrogen blanket with an oxygen sparge. The formation of Crystal Violet

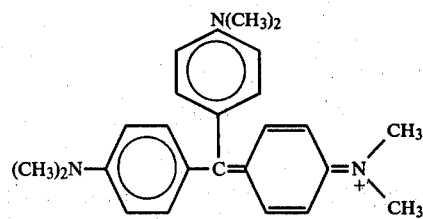

is followed spectroscopically, using the following procedure:

sample weight—0.46 g, diluted to 25 ml with acetic acid. A 25 ml aliquot is then diluted to 2000 ml with water. The absorbance is measured at 590 nm.

When the absorbance, as measured by the above procedure, does not increase, the product is worked up by downing the reaction mass in ammonium hydroxide as in B below.

B. Isolation of Crystal Violet as the Carbinol

The reaction mixture is poured into 500 ml of concentrated ammonium hydroxide solution containing 500 ml of ice. The slurry is stirred for 1 hour, filtered, the filter cake washed in 50 ml of dilute ammonium hydroxide and then dried in a vacuum oven at 50° C.

EXAMPLE 26

Acetic acid (10 g), 34.6 g Fischer's base,

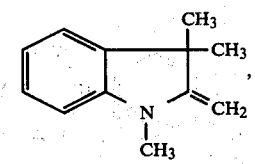

10 g formamidine acetate, and 25 g acetic anhydride are stirred together at room temperature under a nitrogen blanket. A rise in temperature is observed and within a few hours the reaction medium becomes quite viscous. After stirring overnight the resulting solution is found to contain the red dye

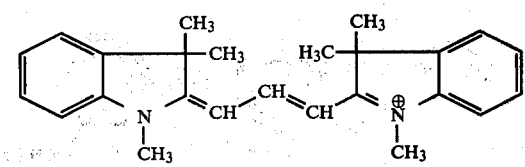

I claim:

1. A process comprising reacting an aromatic compound Ar, wherein Ar is selected from the group consisting of

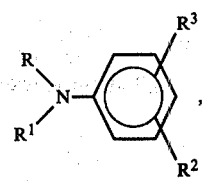

where —R is —CH₃, —C₂H₅, —CH₂CH₂CN, —CH₂CH₂OH, —CH₂CH₂OCH₃, —CH₂CH₂N(CH₃)₂ or —CH₂CH=CH₂, —R¹ is —R or —R² is —H, —CH₃ —C₂H₅, —OCH₃, —OC₂H₅, or

[structure: phenyl with —NHC(O)CH₃]

and R³ is —H, —CH₃, —OCH₃ or —OC₂H₅;

[structures: phenylhydrazone with CH₃ and C=O; pyrrole;
furan-triazole; thiophene; indole;
carbazole; morpholine-cyclohexenyl;
hydroxymethyl-methylene indoline fused to cyclohexane, CH₃CCH₂C(O)NH-phenyl;
anthracene, dimethoxybenzene, or
1-naphthol]

with a compound of the formula H₂NCH=NH⁺ CH₃CO₂⁻; and an anhydride of the formula (CH₃C)₂O, (CF₃C)₂O, (ClCH₂C)₂O, (CH₃CH₂C)₂O,
    ‖        ‖         ‖          ‖
    O        O         O          O (CH₃CH₂CH₂C)₂O  or  [succinic anhydride structure],
         ‖
         O to form a compound of the formula $$Ar_mCH(NHCCA_3)_{3-m}$$
         ‖
         O where A is H or F and m is 1, 2, or 3.

2. The process of claim 1 wherein the reaction is carried out in a nonpolar organic solvent.

3. The process of claim 2 wherein the reaction is carried out at from 25° to 40° C.

4. The process of claim 3 wherein A is —CH₃ and the anhydride is (CH₃C)₂O.
    ‖
    O 5. The process of claim 4 wherein m is 1.

6. The process of claim 5 wherein Ar— is (CH₃)₂N—[phenyl].

7. The process of claim 5 wherein the compound

ArCH(NHCCH₃)₂
       ‖
       O is hydrolyzed to ArCHO.

8. The process of claim 7 wherein Ar— is (CH₃)₂N—[phenyl].

9. The process of claim 3 wherein m is 2.

10. The process of claim 9 wherein Ar— is (CH₃)₂N—[phenyl].

11. The process of claim 3 wherein m is 3.

12. The process of claim 11 wherein Ar— is (CH₃)₂N—[phenyl].

* * * * *